US009211265B2

(12) United States Patent
Storm

(10) Patent No.: US 9,211,265 B2
(45) Date of Patent: Dec. 15, 2015

(54) TABLETS COMPRISING A TASTE MASKING AGENT

(75) Inventor: Klaus Storm, Holzkirchen (DE)

(73) Assignee: HEXAL AG, Holzkirchen (DE)

( * ) Notice: Subject to any disclaimer, the term of this patent is extended or adjusted under 35 U.S.C. 154(b) by 282 days.

(21) Appl. No.: 13/393,779

(22) PCT Filed: Apr. 12, 2010

(86) PCT No.: PCT/EP2010/054759
§ 371 (c)(1),
(2), (4) Date: May 14, 2012

(87) PCT Pub. No.: WO2010/119009
PCT Pub. Date: Oct. 21, 2010

(65) Prior Publication Data
US 2012/0220628 A1 Aug. 30, 2012

(30) Foreign Application Priority Data

Apr. 17, 2009 (EP) .................................... 09158107

(51) Int. Cl.
A61K 31/445 (2006.01)
A61K 9/70 (2006.01)
A61K 9/00 (2006.01)
A61K 9/20 (2006.01)

(52) U.S. Cl.
CPC ............. *A61K 9/7007* (2013.01); *A61K 9/0056* (2013.01); *A61K 9/2018* (2013.01); *A61K 31/445* (2013.01)

(58) Field of Classification Search
USPC ........................................................ 514/319
See application file for complete search history.

(56) References Cited

U.S. PATENT DOCUMENTS 3,917,853 A * 11/1975 Greenshields ................... 426/60
6,576,677 B1 * 6/2003 Ukai et al. ................. 514/772.4
2002/0110581 A1 8/2002 Ream et al.
2007/0207205 A1 * 9/2007 Equipart ....................... 424/464

OTHER PUBLICATIONS

Keast (Bitterness Suppression with Zinc Sulfate and Na-Cyclamate: A Model of Combined Peripheral and Central Neural Approaches to Flavor Modification, Pharmaceutical Research, Kluwer Academic Publishers—Plenum Publishers, NE, vol. 22, No. 11, Nov. 1, 2005, pp. 1970-1977).*
Worldwide Approval Status of Cyclamate, Calorie Control Council, Sep. 29, 2009.*
Russell S. J. Keast, et al., "Bitterness Suppression with Zinc Sulfate and Na-Cyclamate: A Model of Combined Peripheral and Central Neural Approaches to Flavor Modification", Pharmaceutical Research, Kluwer Academic Publishers—Plenum Publishers, NE, vol. 22, No. 11, Nov. 1, 2005, pp. 1970-1977.
Russell S. J. Keast, et al., "Oral Zinc Sulfate Solutions Inhibit Sweet Taste Perception", Chemical Senses Jul. 2004, vol. 29, No. 6, Jul. 2004, pp. 513-521.
Russell S. J. Keast, "The Effect of Zinc on Human Taste Perception", Journal of Food Science, vol. 68, No. 5, Jun. 2003, pp. 1871-1877.
M. J. Gardner, et al., "Zn(II)-Theophylline-Ethylenediamine: Structure of pH Stability", Journal of Pharmaceutical Sciences Apr. 1983, vol. 72, No. 4, Apr. 1983, pp. 348-350.
Russell S. J. Keast, et al., "Modifying the Bitterness of Selected Oral Pharmaceuticals With Cation and Anion Series of Salts", Pharmaceutical Research, Kluwer Academic Publishers, New York, NY, US, vol. 19, No. 7, Jul. 1, 2002, pp. 1019-1026.
T. Yoshida, et al., "Salting-Out Taste-Masking System Generates Lag Time With Subsequent Immediate Release", International Journal of Pharmaceutics, Elsevier BV, NL, vol. 365, No. 1-2, Jan. 5, 2009, pp. 81-88.

* cited by examiner

Primary Examiner — Adam C Milligan
(74) Attorney, Agent, or Firm — Arent Fox LLP

(57) ABSTRACT

The present invention is directed to a tablet comprising at least one bitter tasting and/or mucosa numbness causing pharmaceutically active compound; and at least one zinc salt. In addition, the present invention relates to the use of a zinc salt to reduce or mask the bitter taste of or the numbness of the mucosa caused by pharmaceutically active compounds.

13 Claims, No Drawings

TABLETS COMPRISING A TASTE MASKING AGENT

CROSS-REFERENCE TO RELATED APPLICATION

This application is a National Stage entry of International Application No. PCT/EP2010/054759, filed Apr. 12, 2010, which claims priority to European Application Nos. 09158107.4, filed Apr. 17, 2009, the entire specifications, claims and drawings of which are incorporated herewith by reference.

The present invention relates to tablets comprising at least one bitter tasting and/or mucosa numbness causing pharmaceutically active compound; and at least one zinc salt, as well as to the use of zinc salts to mask the taste of active ingredients in pharmaceutical formulations, in particular tablets, that have a bitter taste or that produce numbness of the mucosa.

An unpleasant characteristic of a variety of active ingredients have a bitter taste and/or produce numbness of the mucosa. This affects particularly those dosage forms which are intended to release the active ingredient immediately, such as orally ingested solutions, oral disintegrating tablets or oral films. To mask the taste of bitter-tasting compounds, a number of methods have been developed in the pharmaceutical industry.

The most common method for masking bitterness is to use a flavouring agent. This is effective for mildly bitter compounds but with highly bitter compounds a heavy, unpleasant, aftertaste is often experienced although a flavouring agent is used. Furthermore, there is a risk that non-homogenous mixing of the bitter compound and flavouring agent can lead to localised areas of bitterness in the mouth when ingested.

The use of zinc, magnesium and sodium salts as an inhibitor of bitterness is discussed in Keast et. al., Pharmaceutical Research, Vol. 22, No. 11, Nov. 2005, p. 1970-1977. The paper assesses the effect of four metal salts on the bitterness of six bitter-tasting compounds, in solution. The results show that, in solution, the effect of the salts on the bitterness of compounds is dependent on both the salt, and the compound. However, an influence on the perception of bitter tasting and/or astringent pharmaceutical compounds has not been demonstrated.

EP 0 974 366 relates to the use of an anionic acidic polysaccharide, such as carrageenan, chondroitin sulphate, dextran sulphate, alginic acid, gellan gum or xanthan gum to mask the bitter taste of a medicine. The examples show the use of an anionic acidic polysaccharide, in a ratio of at least 1:1 with the bitter tasting medicine, in the manufacture of granules, jellies and syrups. Although a masking effect of the bitter medicine is shown, the quantity of anionic acidic polysaccharide required to achieve this is relatively high.

J. Szejtli and L. Szente disclosed the use of a cyclodextrin such as β-cyclodextrin to form an inclusion complex with a bitter tasting component to strongly reduce or eliminate the bitter taste of a substance (Szejtli, J. and Szente, L., Elimination of bitter, disgusting tastes of drugs and foods by cyclodextrins, Eur. J. Pharm. Biopharm. 61, 115-25 (2005)). However, the bitter tasting component has to have the appropriate size for forming a stable inclusion complex with the cyclodextrin to allow for a taste masking effect.

U.S. application No. 20070122475 discloses compositions containing a bitter tasting or unpleasant sensations causing medicament and an agent which masks this effect. These taste-masking agents are Carbomer 934, Carbomer 971, Carbomer 974, PEG-5M or mixtures thereof.

The problems with the aforementioned compositions is that they either require high quantities of the taste masking agent and/or they are only effective in dosage forms that are less practical with respect to storage and administration.

The present invention addresses these problems by providing a tablet composition comprising at least one bitter tasting and/or mucosa numbness causing pharmaceutically active compound and at least one zinc salt.

It has been surprisingly found that a low quantity of a zinc salt, relative to the bitter tasting pharmaceutical compound, is sufficient to mask the taste of bitter pharmaceutically active compounds when formulated into a tablet.

A further aspect of the composition according to the present invention is that the addition of a zinc salt not only masks the bitter taste, but it can also reduce the numbness of the mucosa experienced when pharmaceutically active compounds get in contact with the mucosa, such as the tongue, mouth and throat mucosa.

In a preferred embodiment of the invention the ratio of bitter tasting and/or mucosa numbness causing active compounds to zinc salts is from about 2:1 to about 5:1 by weight (i.e. w/w), more preferably from about 2.5:1 to about 4:1 by weight, such as from 2.8:1 to 3:1 by weight, or alternatively from 3:1 to about 3.5:1 by weight.

Furthermore, the molar ratio of bitter tasting and/or mucosa numbness causing active compounds to zinc ions is preferably from about 0.5:1 to about 2:1, more preferably from about 1:1 to about 1.5:1, particularly around 1.2:1.

The tablets of the present invention may contain any bitter tasting pharmaceutically active compound including, but not limited to, donepezil hydrochloride, dextromethorphan, chlorhexidine, guaifenensin, pseudoephedrine, caffeine, atorvastatin, acetyl salicylic acid, acetaminophen, diphenhydramine, doxylamine, sildenafil citrate, loperamide, midodrine hydrochloride, brotizolam, ticlopidine hydrochloride, maprotiline hydrochloride, iphenprodil tartrate, berberine hydrochloride, digitoxin, sulpyrine, azelastine hydrochloride, etilefrine hydrochloride, diltiazen hydrochloride, propranolol hydrochloride, chloramphenicol, aminophylline, erythromycin, phenobarbital, calcium pantothenate or pantothenic acid, indeloxazine hydrochloride, aminoguanidine hydrochloride, ibuprofen and cefcapene hydrochloride.

The zinc salt of the present invention may be, e.g., zinc chloride, zinc bromide, zinc iodide, zinc sulphate and/or zinc acetate, although other zinc salts may be suitable.

Of course, it is within the scope of the present invention to use zinc salts together with other taste-masking agents. However, to profit best from the merits of the present invention, it is recommended that the taste-masking agents different from zinc salts amount to less than 50%, preferable less than 20%, most preferable less than 10% by weight of the total taste-masking agents.

The tablets of the present invention may comprise additional excipients well known in the art, including e.g. fillers, binders, lubricants, sweeteners and flavouring agents.

Preferred fillers include, but are not limited to microcrystalline cellulose, mannitol, starch or a mixture of various starches, sorbitol, glucose and lactose. Appropriate binders can include, e.g., hydroxypropylmethylcellulose (HPMC), polyvinylpyrrolidon (PVP) and/or starches, modified or not. Suitable sweeteners may e.g. be selected from sucralose, thaumatin, neohesperidine aspartame, sodium cyclamate, saccharin, acesulfame or mixtures thereof such as aspartame and acesulfame salt; various flavouring agents which may be used include e.g. lemon, orange, grapefruit, berry flavours, peppermint or menthol, just to name a few.

In one particular embodiment of the present invention, the tablet is in the form of an oral disintegrating tablet. These oral disintegrating tablets further contain one or more disintegrants. Preferred disintegrants to be used in the oral disintegrating tablets include, e.g. sodium croscarmellose and/or sodium starch glycolate, although other disintegrants may equally be suitable.

However, it was unexpectedly found, that particular disintegrants are more suitable for the combination with a certain pharmaceutically active ingredient to achieve the reduction in bitterness and/or numbness by the use of zinc salts. E.g., sodium croscarmellose and sodium starch glycolate prove to be more suitable for a combination with donepezil-HCl and $Zn^2$ than crospovidone. However, for other combinations of pharmaceutically active ingredients and zinc salts, standard commercially available crospovidone is equally suitable to produce the effect of the tablet compositions of the present invention as other disintegrants such as sodium croscarmellose or sodium starch glycolate are. An oral disintegrating tablet comprising at least one of these disintegrants, a zinc salt and a pharmaceutically active ingredient non-susceptible to oxidation, such as e.g. ticlopidine hydrochloride or ibuprofen, may be such an example.

As previously mentioned, the tablets according to the present invention do not just allow to mask the bitter taste of its constituents, usually the active ingredients, but also for the reduction of a numbness occurring when the active ingredient contacts the mucosa. The reason for this reduction or even complete avoidance of this numbness is not yet fully understood. Without being bound to this theory, it is assumed that the astringent effect of $Zn^2$ salts contributes to this unexpected effect.

The taste-masking effect of the compositions according to the invention is particularly surprising as this effect is specific to tablets such as oral disintegrating tablets. In other pharmaceutical formulations, such as oral films, the addition of a zinc salt does not mask the bitter taste of an active ingredient such as donepezil hydrochloride (see reference examples below).

The tablets according to the invention are further characterized by their good storage stability.

The present invention is described in more detail in accordance with the following example but the scope of the present invention is not limited to this example.

EXAMPLES

Reference Example 1

Oral films were prepared according to the following process:

The active ingredient donepezil hydrochloride is dissolved in solvent. Subsequently filling material, plasticizer, pigments and taste masking agents are added. Finally the film-forming polymer (Methocel E5LV) is added. After swelling of the polymer, the mass is cast on a thin foil. The material is dried so that the solvent is quantitatively removed, and after removing the thin foil a thin API-containing film is obtained.

The final composition of the obtained film is shown in Table 1 below:

TABLE 1

|  | % by wt. | mg |
|---|---|---|
| Active ingredient |  |  |
| Donepezil Hydrochloride | 20.83 | 1.167 |
| Excipients |  |  |
| Methocel E5LV | 30.00 | 1.680 |
| Glycerol (85%) | 16.00 | 0.896 |

TABLE 1-continued

|  | % by wt. | mg |
|---|---|---|
| Avicel PH 101 | 17.17 | 0.961 |
| Maltodextrine | 15.00 | 0.840 |
| Zinc sulphate | 1.00 | 0.056 |

Reference Example 2

Oral films were prepared according to the same process as in Reference Example 1 using the composition shown in Table 2 below:

TABLE 2

|  | % by wt. | mg |
|---|---|---|
| Active ingredient |  |  |
| Donepezil Hydrochloride (Form III) | 20.83 | 1.500 |
| Excipients |  |  |
| Methocel E5LV | 30.00 | 2.160 |
| Glycerol (85%) | 20.00 | 1.440 |
| Avicel PH 101 | 12.88 | 0.927 |
| Maltodextrin | 9.00 | 0.648 |
| Zinc sulphate | 7.29 | 0.525 |

The oral films of both Reference Examples were tested by 7 volunteers each (aged 25-47, 3 male, 4 female), none of whom observed a significant reduction in the bitterness of the pharmaceutical compound.

Example 1

Donepezil hydrochloride, mannitol, zinc sulphate monohydrate, peppermint flavour, aspartame, aerosil, microcrystalline cellulose and sodium croscarmellose were sieved and mixed in the quantities shown in Table 3. The mixture was then sieved prior to mixing with sieved magnesium stearate. Subsequently, the resulting mixture was compressed into oral disintegrating tablets.

TABLE 3

| Raw material | Quantity for 1 dose of 5 mg strength (mg/tablet) | Quantity for 1 dose of 5 mg strength (% by wt.) | Reference tablet (mg/tablet) | Reference tablet (% by wt.) |
|---|---|---|---|---|
| Donepezil-HCl | 5.00 | 1.786 | 5.00 | 1.786 |
| Pearlitol 100 SD (Mannitol Spraydried) | 199.05 | 71.089 | 200.80 | 71.714 |
| MCC 90µ (Microcrystalline cellulose) | 28.00 | 10.00 | 28.00 | 10.00 |
| Aspartame | 8.40 | 3.00 | 8.40 | 3.00 |
| Aerosil 200 | 11.20 | 4.00 | 11.20 | 4.00 |
| Ac-Di-Sol (Sodium Croscarmellose) | 19.60 | 7.00 | 19.60 | 7.00 |
| Peppermint flavor | 2.80 | 1.00 | 2.80 | 1.00 |
| Zinc sulphate monohydrate | 1.75 | 0.625 | — | — |
| Mg-stearate | 4.20 | 1.5 | 4.20 | 1.5 |
| total | 280.00 | 100 | 280.00 | 100 |

The same 7 volunteers (aged 25-47, 3 male, 4 female) tasted oral disintegrating tablets with and without zinc sulphate.

Result: All 7 individuals assessed the tablets containing zinc sulphate as much less bitter than the control tablets

The invention claimed is:

1. A method of reducing or masking the bitter taste of one or more pharmaceutically active compounds provided in an oral solid dosage form comprising:
   providing a pharmaceutical composition comprising one or more pharmaceutically active compounds having a bitter taste; and
   adding at least one zinc salt to mask the bitter taste of the one or more pharmaceutically active compounds in the pharmaceutical composition,
   wherein the ratio of the one or more pharmaceutically active compounds having a bitter taste to the at least one zinc salt is from 2:1 to 5:1 by weight.

2. A method of reducing or masking the numbness of the mucosa caused by one or more pharmaceutically active compounds provided in an oral solid dosage form comprising:
   providing a pharmaceutical composition comprising one or more pharmaceutically active compounds that cause numbness of the mucosa; and
   adding at least one zinc salt to mask the numbness of the mucosa caused by theone or more pharmaceutically active compounds in the pharmaceutical composition,
   wherein the ratio of the one or more pharmaceutically active compounds that cause numbness of the mucosa to the at least one zinc salt is from 2:1 to 5:1 by weight.

3. The method of claim 1, wherein the one or more pharmaceutically active compounds also causes numbness and the method of reducing or masking the bitter taste of the one or more pharmaceutically active compounds also reduces or masks numbness.

4. A method of reducing or masking the bitter taste of one or more pharmaceutically active compounds provided in an oral solid dosage form comprising:
   providing a pharmaceutical composition comprising one or more pharmaceutically active compounds having a bitter taste; and
   adding at least one zinc salt to mask the bitter taste of the one' or more pharmaceutically active compounds in the pharmaceutical composition,
   wherein the ratio of the one or more pharmaceutically active compounds having a bitter taste to the at least one zinc salt is from about 2.5:1 to about 5:1 by weight.

5. The method of reducing or masking the bitter taste of one or more pharmaceutically active compounds of claim 4, wherein the ratio of the one or more pharmaceutically active compounds having a bitter taste to the at least one zinc salt is from 2.8:1 to about 5:1 by weight.

6. A method of reducing or masking the numbness of the mucosa caused by one or more pharmaceutically active compounds provided in an oral solid dosage form comprising:
   providing a pharmaceutical composition comprising one or more pharmaceutically active compounds that cause numbness of the mucosa; and
   adding at least one zinc salt to mask the numbness of the mucosa caused by the one or more pharmaceutically active compounds in the pharmaceutical composition,
   wherein the ratio of the one or more pharmaceutically active compounds that cause numbness of the mucosa to the at least one zinc salt is from about 2.5:1 to about 5:1 by weight.

7. The method of reducing or masking the numbness of the mucosa caused by one or more pharmaceutically active compounds of claim 6, wherein the ratio of the one or more pharmaceutically active compounds that cause numbness of the mucosa to the at least one zinc salt is from 2.8:1 to about 5:1 by weight.

8. The method of claim 1, wherein the oral solid dosage form is an oral disintegrating tablet.

9. The method of claim 8, wherein the active agent is donepezil hydrochloride, and the oral disintegrating tablet comprises a disintegrant selected from the group consisting of sodium croscarmellose, sodium starch glycolate, and combinations thereof.

10. The method of claim 4, wherein the oral solid dosage form is an oral disintegrating tablet.

11. The method of claim 10, wherein the active agent is donepezil hydrochloride, and the oral disintegrating tablet comprises a disintegrant selected from the group consisting of sodium croscarmellose, sodium starch glycolate, and combinations thereof.

12. The method of claim 6, wherein the oral solid dosage form is an oral disintegrating tablet.

13. The method of claim 12, wherein the active agent is donepezil hydrochloride, and the oral disintegrating tablet comprises a disintegrant selected from the group consisting of sodium croscarmellose, sodium starch glycolate, and combinations thereof.

* * * * *